United States Patent [19]

Hyon et al.

[11] Patent Number: 5,227,412
[45] Date of Patent: Jul. 13, 1993

[54] BIODEGRADABLE AND RESORBABLE SURGICAL MATERIAL AND PROCESS FOR PREPARATION OF THE SAME

[75] Inventors: Suong-Hyu Hyon; Yoshito Ikada, both of Uji; Yasuo Shikinami, Kusatsu; Kaoru Tsuta, Hyogo; Hidekazu Boutani, Himeji, all of Japan

[73] Assignees: Biomaterials Universe, Inc., Kyoto; Takiron Co., Ltd., Osaka, both of Japan

[21] Appl. No.: 944,019

[22] Filed: Sep. 14, 1992

Related U.S. Application Data

[63] Continuation of Ser. No. 415,205, Sep. 14, 1989, abandoned.

[30] Foreign Application Priority Data

Dec. 28, 1987 [JP] Japan .................. 62-333333

[51] Int. Cl.$^5$ ................. C08J 3/00; C08K 5/15; C08L 67/04
[52] U.S. Cl. ................... 523/105; 525/415
[58] Field of Search ............. 523/105; 525/415

[56] References Cited

U.S. PATENT DOCUMENTS 4,279,249  7/1981  Vert et al. .................. 525/415
4,898,186  2/1990  Ikada et al. ................. 525/415

FOREIGN PATENT DOCUMENTS

0199074A1  10/1986  European Pat. Off.
0202090A2  11/1986  European Pat. Off.

OTHER PUBLICATIONS

Michael Vert et al, Makromol. Chem., Suppl. 5, pp. 30–41 (1981).
D. C. Tunc, Transactions of Ninth Annual Meeting of The Society for Biomaterials, p. 47 (1983).
P. Törmälä et al, Biomaterials, 8, pp. 42–45 (1987).
Jan. W. Leenslag et al, Biomaterials 8, pp. 70–73 (1987).

*Primary Examiner*—Thurman K. Page
*Assistant Examiner*—U. K. Rajguru
*Attorney, Agent, or Firm*—Armstrong, Westerman, Hattori, McLeland & Naughton

[57] ABSTRACT

Biodegradable and resorbable surgical materials of molded articles of poly(lactic acid) or copolymers of lactic acid and glycolic acid, characterized in that the articles are molecular-orientated, and having a bending strength of $1.6 \times 10^{33}$ to $2.5 \times 10^3$ kg/cm$^2$, a bending modulus of $5.5 \times 10^2$ to $24.0 \times 10^2$ kg/cm$^2$, a crystallinity, determined by density measurement, of 10 to 60%, and a viscosity average molecular weight measured after melt processing of not less than 200,000, and in that at least 80% of initial strength of the articles is maintained after dipping in a saline at 37° C. for three months.

4 Claims, No Drawings

BIODEGRADABLE AND RESORBABLE SURGICAL MATERIAL AND PROCESS FOR PREPARATION OF THE SAME

This application is a continuation of application Ser. No. 415,205 filed Sep. 14, 1989, now abandoned.

DESCRIPTION

1. Technical Field

The present invention relates to biodegradable and resorbable surgical materials based on poly(lactic acid) having an excellent mechanical strength, a hydrolytic resistance, and a process for preparation of the same.

2. Background Art

In the fields of orthopaedic surgery and oral surgery, bone plates, and small screws having a high strength are used for treating fractured portions of bone. These materials should function during fracture healing. However, after healing it is necessary to remove them in early stage in order to prevent the healed bone from weakening.

At present, almost of all bone plates, and the like, commonly applied in clinical use are made of metals. Recently, ceramic plates were introduced. However, because of the high elastic modulus bone deterioration is a problem. Furthermore, elution of metal ions causes damage to the human body. Accordingly, if it is desired to have surgical devices made of materials with an elastic modulus equal to or slightly higher than that of bones which are biodegradable and resorbable. Such materials will eliminate the need for a second operation to remove the implant. Also, various adverse effects due to the long time presence of foreign materials in the body can be eliminated.

In response to the above requirements, aggressive development of such devices using biodegradable and resorbable materials such as poly(lactic acid) and lactic acid-glycolic acid copolymers has been proceeded.

For example, M. Vert, F. Chabot et al synthesize poly(lactic acid) and lactic acid-glycolic acid copolymers for use as bone plates and reported a 100% poly(lactic acid) having a bending modulus of 3.4 GPa (340 kg/mm$^2$) (Makromol Chem. Suppl., 5, 30–41, 1981). Also D. C. Tunc reported a bone plate of poly(lactic acid) having a bending modulus of 520 kg/mm$^2$ (TRANSACTIONS of Ninth Annual Meeting of The Society for Biomaterials of USA, 6, 47, 1983).

In addition, Japanese Tokkyo Kokai No. 97654/1984 discloses a process for preparing poly(lactic acid) used as resorbable materials for fixation devices of bone fractures. The poly(lactic acid), however, has a low tensile strength of about 580 kg/cm$^2$, and there are no explanation as to a molding and processing method of poly(lactic acid).

Recently, a composite bone plate of a glycolic acid-lactic acid copolymer reinforced with fibers of a glycolic acid-lactic acid copolymer has been developed. The plate, however, has a low bending modulus of 265 MPa (26.5 kg/mm$^2$), which further bending modulus rapidly decreased with hydrolysis in vitro to make it weaken for about one month (P. Tormala et al, Biomaterials, 8, 42, 1987). Also J. W. Leenslag, A. J. Pennings et al synthesized a poly(lactic acid) having a viscosity average molecular weight of about one million. They reported that a bone plate from this poly(lactic acid) has a bending modulus of 5 GPa (500 kg/mm$^2$) (Biomaterials, 8, 70, 1987). However, since the poly(lactic acid) has such a high molecular weight, processability thereof is poor.

As described above, many studies have been reported and various methods have been tried, for improving mechanical properties of osteosynthetic devices of poly(lactic acid). As of yet, no material has been developed, having sufficient strength for clinical use.

The present invention has been accomplished under the above background arts, and can provide biodegradable and resorbable surgical materials having a high strength and a high hydrolytic resistance which are largely improved in comparison with the mechanical properties and hydrolytic resistance of the prior known osteosynthetic devices of poly(lactic acid).

As a result of the inventors' intensive studies for achieving the above objects, it was surprisingly found that poly(lactic acid), or copolymers of lactic acid and glycolic acid, having a viscosity average molecular weight of not less than 300,000 can maintain their viscosity average molecular weight at a level of not less than 200,000 by melt-processing, e.g. extrusion molding or compression molding, at a temperature range from their melting point to 220° C. Subsequently, the molded articles are subjected to stretch at a temperature of 60° to 180°, in a nitrogen atmosphere or in an oil in order to preserve them from decreasing in molecular weight due to oxidative decomposition. The materials obtained are tough and hydrolytically resistive surgical materials of poly(lactic acid) having a bending strength of not less than $1.6 \times 10^3$ kg/cm$^2$ and a bending modulus of not less than $5.5 \times 10^2$ kg/mm$^2$, and then the present invention has been completed.

DISCLOSURE OF INVENTION

The present invention is based on the above fact, and is directed toward biodegradable and resorbable surgical materials which are the molded articles of poly(lactic acid) or copolymers of lactic acid and glycolic acid having a molecular-orientation, and further characterized in that a bending strength is $1.6 \times 10^3$ to $2.5 \times 10^3$ kg/cm$^2$, preferably $1.7 \times 10^3$ to $2.3 \times 10^3$ kg/cm$^2$, a bending modulus is $5.5 \times 10^2$ to $24.0 \times 10^2$ kg/mm$^2$, preferably $6.0 \times 10^2$ to $20.0 \times 10^2$ kg/mm$^2$, a crystallinity determined by density measurement is 10 to 60%, a viscosity average molecular weight measured after melt processing is not less than 200,000, and at least 80%, preferably at least 90% of initial strength is maintained after dipping in a saline solution at 37° C for three months. The invention discloses a process for preparing the same which is characterized by melt-processing poly(lactic acid) or copolymers of lactic acid and glycolic acid having a viscosity average molecular weight of 300,000 to 600,000 at a temperature range from their melting point to 220° C., and then stretching the molded articles at a temperature of 60° to 180° C.

BEST MODE FOR CARRYING OUT THE INVENTION

The poly(lactic acid) used in the present invention is prepared by synthesizing a lactide which is a cyclic dimer of lactic acid according to a well known method (C. E. Lowe, U.S. Pat. No. 2,668,162) from an optically active L- or D-lactic acid, and then subjecting the lactide to a ring-opening polymerization. Since this poly(lactic acid) has poor heat stability, it is necessary that its viscosity average molecular weight be not less than 300,000 by taking into account molecular degradation during the melt-processing. A poly(lactic acid) having a higher molecular weight can give a surgical material having a higher strength. When a poly(lactic acid) with a too high molecular weight is used, however, the melt-processing must be carried out at a high temperature under a high pressure which will cause the molecular weight to decrease to a great extent. As a result, the molecular weight decreases to below 200,000 after the melt-processing, and thus the desired surgical material having a high strength can hardly be obtained. Accordingly, a poly(lactic acid) having a viscosity average molecular weight of 300,000 to 600,000, preferably 350,000 to 550,000, particularly 400,000 to 500,000 is most suitable.

Also, in the present invention, a lactic acid-glycolic acid copolymer may be used instead of the above poly(lactic acid). This copolymer has the same molecular weight as that of the poly(lactic acid), and can be prepared according to a well known method. Particularly copolymers having a greater content of lactic acid are suitable, and among them copolymers having a weight ratio of lactic acid/glycolic acid of 99/1 to 75/25 are preferably used. When the glycolic acid content is small and within the above range, the obtained surgical material is scarcely degraded even if the material is dipped in a saline at 37° C. for three months, because the surgical material has an excellent hydrolytic resistance. When the glycolic acid content is increased beyond the above range, there arises a disadvantage that the material looses its strength in an early stage due to the lowering of the molecular weight.

The surgical material of the present invention can be prepared by using the above poly(lactic acid) or the lactic acid-glycolic acid copolymer (hereinafter referred to as "copolymer") as a starting material, subjecting the polymer to melt-processing, e.g. extrusion molding or press molding to give it an optional shape such as rod or web, and then uniaxially stretching the molded article in the direction of the main axis. This melt extrusion molding has a good productivity, and can be carried out by using an ordinary extrusion machine under the following temperature and pressure conditions.

Namely, it is necessary to control a melt extrusion temperature in a temperature range from a melting point of the above poly(lactic acid) or the copolymer (about 175° to 185° C.) to 220° C., preferably the melting point to 215° C. The melt extrusion molding is difficult to carry out at a temperature of below the melting point. On the other hand, when carrying out at a temperature of more than 220° C., the molecular weight of the poly(lactic acid) or the copolymer is drastically decreased, and the viscosity average molecular weight of the melt-processed article becomes less than 200,000. Preferred molecular weight of the melt-processed article is not less than 200,000, particularly 250,000 to 400,000. When a molecular weight of the article is less than 200,000, improvement of dynamical properties cannot be expected even by stretching. In order to reduce the decrease of the molecular weight to a minimum, it is important to carry out the melt-extrusion molding at a slightly higher temperature than the melting point of the starting polymer. Accordingly, when using the above-mentioned polymer having a molecular weight of 400,000 to 500,000 as a starting polymer, the melt-extrusion molding is desirably carried out at a temperature of not more than 200° C. In addition, after the molding a higher molecular weight is preferred in order to obtain high mechanical properties, but if the molecular weight is too high processability becomes poor.

Similarly, with respect to the pressure conditions of the melt-extrusion molding, as related to controlling the molecular weight decrease as low as possible, it is desirable that the extrusion pressure is regulated to a minimum extrudable pressure for the viscosity (molecular weight) of the molten starting polymer. Accordingly, when a molecular weight of the starting polymer is up to 600,000, a suitable extrusion pressure is not more than 260 kg/cm$^2$, and when the molecular weight is 400,000 to 500,000, a suitable extrusion pressure is approximately 170 to 210 kg/cm$^2$.

Prior to the melt-extrusion molding, it is preferable to sufficiently dehydrate pellets of the starting poly(lactic acid) or copolymer by drying them with heating under a reduced pressure.

Since the molded articles obtained by the melt-extrusion molding have a viscosity average molecular weight of not less than 200,000, they have a significantly high strength, but do not reach the desired strength. Therefore, according to the present invention, the molded articles are further subjected to a uniaxial stretching in the main axial direction (extrusion direction) in a medium such as a liquid paraffin or a silicone oil, whereby the polymer molecules are orientated to yield articles with improved strength.

It is necessary to carry out the uniaxial stretching at a temperature of 60° to 180° C., preferably 80° to 160° C. When the temperature is lower than 60° C., a glass transition point of the starting polymer is so near that the molecular orientation by stretching becomes insufficient. On the other hand, when the temperature is higher than 180° C., the molecular weight of the polymer becomes low. Therefore, in both cases it is difficult to sufficiently improve the strength by stretching. Preferred temperature of stretching varies depending on the molecular weight of the molded polymer such that if the molecular weight is approximately 200,000 to 250,000, the temperature is approximately 100° C.

The desired stretching ratio is 2 to 6. When the stretching ratio is smaller than 2, it is difficult to obtain a satisfactory strength because of insufficient molecular orientation. On the other hand, when the ratio is larger than 6, the hydrolytic resistance is lowered because of fibrillation. The stretching temperature is necessarily controlled so that a crystallinity of the molded article is 10 to 60%, preferably 20 to 50%. Though a crystallinity of a molded article can generally give a higher dynamic strength, a molded article of poly(lactic acid) having a too high crystallinity is inferior with respect to hydrolytic resistance. On the other hand, when the crystallinity is lower than 10%, the desired strength and modulus cannot be obtained.

The thus obtained uniaxially stretched articles are cut to a given length, and then are subjecting to cutting work to provide final products having various size and shape, e.g. bone plates, pins, small screws or machinal screws which may be used in clinical fields of orthopaedic surgery, oral surgery, thoracic surgery, or the like.

The surgical materials of the present invention prepared by the above-mentioned process have the biodegradable and resorbable properties because they are made of the poly(lactic acid) or the copolymers of lactic acid and glycolic acid, and therefore there is little anxiety about bad influences in a living body like conventional metallic surgical materials. In addition, since the surgical materials of the present invention have a viscosity average molecular weight of not less than 200,000 even after the melt-extrusion molding by inhibiting the decrease of molecular weight to a minimum, in addition to having a high molecular orientation and crystal orientation by stretching, the surgical materials of the invention have the high strength, i.e. a bending strength of $1.6 \times 10^3$ to $2.5 \times 10^3$ kg/cm$^2$, a bending modulus of $5.5 \times 10^2$ to $24.0 \times 10^2$ kg/mm$^2$, and a crystallinity of 10 to 60%. Those properties cannot be obtained by the conventional poly(lactic acid) surgical materials in combination with the improved hydrolytic resistance where the strengths is scarcely decreased during dipping in a saline at 37° C. for three months.

The surgical materials of poly(lactic acid) of the present invention are explained by means of the following Examples, but it should be noted that the present invention is not limited to these Examples.

EXAMPLE 1

Pellets of a poly(lactic acid) having an initial viscosity average molecular weight of 420,000 (melting point of about 180° C.) were dried under a reduced pressure at 120° to 140° C. for a day and a night. After the dry pellets were put in an extruder and allowed to stand for about 20 minutes under a reduced pressure, the melt-extrusion molding was carried out under the temperature conditions shown in Table 1 to give a square bar or a round bar. A viscosity average molecular weight of the obtained square bar and round bar were 220,000 as shown in Table 1. The value is calculated according to the following viscosity equation is missing.

$$[\eta] = 5.45 \times 10^{-4} M^{0.73} \; (chloroform \; 25° \; C.)$$

Subsequently, the molded articles were uniaxially stretched twice in the main direction in a liquid paraffin at 100° C., and then were cut to give a test piece (size: 10 mm width, 5 mm thickness, 80 mm length). As a result of measuring a bending strength and a bending modulus of the test piece, the bending strength was 1720 kg/cm$^2$ and the bending modulus was 610 kg/mm$^2$ as shown in Table 1.

Further the test piece was dipped in a saline at 37° C. for three months, and thereafter a bending strength and a bending modulus were measured. The bending strength was 1710 kg/cm$^2$ and the bending modulus was 610 kg/mm$^2$, which shows less degradation of strength. The crystallinity was about 28%.

The above bending strength and the bending modulus were measured according to the method of JIS K-7203, and the crystallinity was calculated from the density measured according to the following method.

Density Measurement

The density was measured at 30° C. by using a density gradient column of n-hexane/carbon tetrachloride system. Prior to the measurement, the test piece was deaerated by immersing for 30 minutes in n-hexane for removing air bubbles.

The crystallinity was calculated from the measured density according to the following equation.

$$\frac{1}{\rho} = \frac{X}{\rho_c} - \frac{1-X}{\rho_a}$$

wherein,
X: crystallinity
$\rho$: measured density of the test piece,
$\rho_c$: density of crystal ($=1.290$ g/cm$^3$),
$\rho_a$: density of amorphous ($=1.248$ g/cm$^3$).

EXAMPLE 2

Test piece was prepared in the same manner as in Example 1 except that a poly(lactic acid) having an initial viscosity average molecular weight of 420,000 (melting point of about 180° C.) was used and the melt-extrusion temperature was set to the temperature shown in Table 1. The bending strength and the bending modulus of both the initial test piece and the test piece after the dipping test in a saline at 37° C. for three months, were measured as well as the viscosity average molecular weight after the melt-extrusion molding, and the crystallinity. The results are shown in Table 1.

EXAMPLE 3

Test piece was prepared in the same manner as in Example 1 except that a lactic acid-glycolic acid copolymer having an initial viscosity molecular weight of 400,000 (lactic acid: glycol acid $=90:10$; melting point of about 180° C.) was used and the melt-extrusion temperature was set to the temperature shown in Table 1. The bending strength and the bending modulus of both of the initial test piece and the test piece after the dipping test in a saline at 37° C. for three months, were measured, as well as the viscosity average molecular weight after the melt-extrusion molding, and the crystallinity. The results are shown in Table 1.

EXAMPLES 4 TO 5

Two kinds of test pieces were prepared in the same manner as in Example 1 except that the stretching temperature was changed to 60° and 160° C., respectively. For each test piece the bending strength and the bending modulus of both of the initial test pieces and the test pieces after the dipping test in a saline at 37° C. for three months, were measured, as well as the viscosity average molecular weight after the melt-extrusion molding, and the crystallinity. The results are shown in Table 1.

COMPARATIVE EXAMPLES 1 TO 2

Two kinds of test pieces were prepared in the same manner as in Example 1 except that a poly(lactic acid) having an initial viscosity average molecular weight of 700,000 (melting point of about 180° C.) and a poly(lactic acid) having an initial viscosity average molecular weight of 280,000 (melting point of about 180° C.) were used and the melt-extrusion temperature was set to the temperature shown in Table 1. With respect to each test piece, the flexural strength and the flexural modulus of both of the initial test piece and the test piece after the dipping test in a saline at 37° C. for three months were measured, as well as the viscosity average molecular weight after the melt-extrusion molding, and the crystallinity. The results are shown in Table 1.

EXAMPLES 6 TO 8

Stretched articles were prepared under the same conditions as in Example 1 except that the stretching ratio was changed to three times, four times and six times. With respect to each stretched article, the bending strength, the bending modulus of both of the initial articles and the articles after the dipping test in a saline at 37° C. for three months, and the density were measured. The results and the crystallinity calculated from the measured density are shown in Table 2.

COMPARATIVE EXAMPLES 3 TO 4

Stretched articles were prepared under the same conditions as in Example 1 except that the stretching was carried out in air at 170° C. and the stretching ratio was changed to seven times and eight times. The same measurements as in Example 6 were carried out. The results are shown in Table 2.

COMPARATIVE EXAMPLE 5

A test piece (non-stretched) was prepared by melt-extrusion molding under the same conditions as in Example 2 from a poly(lactic acid) having an initial viscosity average molecular weight of 420,000 (melting point of about 180° C.). Both of the bending strength and the bending modulus were low, i.e. 1300 kg/cm$^2$ and 450 kg/mm$^2$, respectively. The crystallinity calculated from the measured density was 8%.

having a very high molecular weight, i.e. 700,000, the molecular weight after the melt-extrusion molding becomes lower than 200,000 due to a high melt-extrusion temperature and pressure. Therefore even if the uniaxial stretching is done, the obtained bending strength and bending modulus do not reach the desired values, and thus, enough strength cannot be obtained.

Also since the material of Comparative Example 2 has a molecular weight smaller than 300,000, even if the decrease of molecular weight is inhibited by applying a lower temperature and a lower pressure at the melt-extrusion molding, the molecular weight of the obtained molded article is far less than 200,000. Therefore the desired strength cannot be obtained even by uniaxial stretching.

In addition, since the materials of Comparative Examples 3 and 4 are stretched at a large stretching ratios, the obtained materials have structural defects due to

TABLE 1

| Ex. No. | Starting polymer | Initial $\overline{M}w$ | Extrusion temp. condition (°C.) Cylinder | Adapter | Die | $\overline{M}W$ after melt-extrusion molding |
|---|---|---|---|---|---|---|
| 1 | Poly (lactic acid) | 440,000 | 198 | 200 | 200 | 200,000 |
| 2 | " | 420,000 | 198 | 200 | 200 | 200,000 |
| 3 | Lactic acid-glycolic acid copolymer (90:10) | 400,000 | 198 | 200 | 200 | 200,000 |
| 4 | Poly (lactic acid) | 440,000 | 198 | 200 | 200 | 220,000 |
| 5 | " | 440,000 | 198 | 200 | 200 | 220,000 |
| Comp. Ex. | | | | | | |
| 1 | Poly (lactic acid) | 700,000 | 220 | 250 | 250 | 180,000 |
| 2 | " | 280,000 | 193 | 195 | 195 | 100,000 |

| Ex. No. | Stretching condition Temp. (°C.) | Ratio (times) | Bending strength (kg/cm$^2$) Initial | After dipping for 3 months | Bending modulus (kg/mm$^2$) Initial | After dipping for 3 months | Crystallinity (%) |
|---|---|---|---|---|---|---|---|
| 1 | 100 | 2 | 1720 | 1710 | 610 | 610 | 28 |
| 2 | 100 | 2 | 1680 | 1630 | 590 | 570 | 23 |
| 3 | 100 | 2 | 1650 | 1590 | 570 | 550 | 26 |
| 4 | 60 | 2 | 1700 | 1680 | 590 | 570 | 18 |
| 5 | 160 | 2 | 1680 | 1650 | 570 | 560 | 57 |
| Comp. Ex. | | | | | | | |
| 1 | 100 | 2 | 1530 | 1450 | 540 | 490 | 61 |
| 2 | 100 | 2 | 1420 | 1380 | 500 | 480 | 32 |

TABLE 2

| Example No. | Stretching ratio (times) | Crystallinity (%) | Bending Strength (kg/cm$^2$) Initial | After dipping for 3 months | Bending Modulus (kg/mm$^2$) Initial | After dipping for 3 months |
|---|---|---|---|---|---|---|
| 6 | 3 | 33 | 1830 | 1810 | 730 | 720 |
| 7 | 4 | 49 | 2160 | 2130 | 1620 | 1610 |
| 8 | 6 | 60 | 2450 | 2410 | 2360 | 2330 |
| Comp. Ex. | | | | | | |
| 3 | 7 | 62 | 1640 | 1280 | 530 | 440 |
| 4 | 8 | 65 | 1570 | 0 | 480 | 0 |

From Table 1 and Table 2, each of the surgical materials of the present invention prepared in Examples 1 to 5 and Examples 6 to 8 has a viscosity average molecular weight after melt-extrusion molding not less than 200,000. Further, each piece has an excellent strength such as a bending strength of 1.6×10$^3$ to 2.5×10$^3$ kg/cm$^2$ and a bending modulus of 5.5×10$^2$ to 24.0×10$^2$ kg/mm$^2$, and also has a high hydrolytic resistance so that its strength is scarcely decreased even after the dipping test in a saline for three months.

In contrast, with respect to the material of Comparative Example 1, though there is used a poly(lactic acid) fibrillation and void generation. Therefore, although the crystallinities are apparently increased, the obtained materials are inferior in the initial dynamic properties and the hydrolitic resistance.

INDUSTRIAL APPLICABILITY

As is clear from the above explanation and the results of these Examples, the biodegradable and resorbable materials of the present invention are the high strength materials having a high bending strength and bending modulus which have not been achieved by the conventional poly(lactic acid) surgical materials, and are excellent in hydrolytic resistance. Accordingly these surgical materials may suitably be used as bone plates, screws, pins or small screws in orthopaedic surgery, oral surgery or thoracic surgery. Also, the process of the present invention can easily and efficiently be achieved, without any special apparatus, by adding the uniaxial stretching step to the melt-extrusion molding step which is commonly employed in resin molding field. Therefore, the process is excellent in mass production and workability.

We claim:

1. Biodegradable and resorbable surgical materials of molded articles consisting of either poly(lactic acid) or copolymers of lactic acid and glycolic acid, characterized in that the articles are uniaxially molecular-oriented, and having a bending strength of $1.7 \times 10^3$ to $2.5 \times 10^3$ kg/cm$^2$, a bending modulus of $5.5 \times 10^2$ to $24.0 \times 10^2$ kg/mm$^2$, a crystallinity, determined by density measurement, of 10 to 60%, and a viscosity average molecular weight measured after melt processing at temperatures of from the melting point of the poly(lactic acid) or copolymer to 220° C. of not less than 200,000, and in that at least 80% of initial strength of the articles is maintained after being dipped in a saline at 37° C. for three months.

2. A process for preparing biodegradable and resorbable surgical materials of molded articles consisting of either poly(lactic acid) or copolymers of lactic acid and glycolic acid, comprising melt-processing poly(lactic acid) or copolymers of lactic acid and glycolic acid having a viscosity average molecular weight of 300,000 to 600,000 at a temperature range from their melting point to 220° C. in nitrogen atmosphere under high pressure, and then stretching the molded articles in liquid paraffin or in a silicone oil at a temperature of 60° to 180° C. to induce uniaxial molecular orientation.

3. The biodegradable and resorbable surgical materials of claim 1, which consist of a copolymer of lactic acid and glycolic acid, said copolymer having a weight ratio of lactic acid to glycolic acid of 99:1 to 75:25.

4. The process of claim 2, wherein a copolymer of lactic acid and glycolic acid is melt-processed, said copolymer having a weight ratio of lactic acid to glycolic acid of 99:1 to 75:25.

* * * * *